United States Patent [19]

Shepherd et al.

[11] Patent Number: 5,331,058
[45] Date of Patent: Jul. 19, 1994

[54] POLYMERIZATION OF OLEFINIC-CONTAINING MONOMERS EMPLOYING ANIONIC INITIATORS

[75] Inventors: Neil Shepherd, Waltham Abbey; Malcolm J. Stewart, Henlow, both of England

[73] Assignee: The Secretary of State for Defence in her Britannic Majesty's Government of the U.K. of Gt. Britain and Northern Ireland, London, England

[21] Appl. No.: 920,368

[22] PCT Filed: Feb. 6, 1991

[86] PCT No.: PCT/GB91/00187

§ 371 Date: Aug. 17, 1992

§ 102(e) Date: Aug. 17, 1992

[87] PCT Pub. No.: WO91/12277

PCT Pub. Date: Aug. 22, 1991

[30] Foreign Application Priority Data

Feb. 8, 1990 [GB] United Kingdom ............... 9002804.4

[51] Int. Cl.[5] .......................... C08F 8/42; C08F 8/34; C08F 8/32; C08F 4/46
[52] U.S. Cl. ............................ 525/332.3; 525/333.2; 525/343; 525/348; 525/359.1; 525/360; 525/367; 525/383; 525/379; 525/385; 525/386; 526/173; 526/178; 526/335; 526/348
[58] Field of Search ............... 526/173, 180, 279, 335, 526/178, 194; 525/272, 332.3, 333.2, 343, 348, 354, 360, 367, 379, 383, 385, 386, 359.1

[56] References Cited

U.S. PATENT DOCUMENTS

| | | | |
|---|---|---|---|
| 3,324,089 | 6/1967 | Trepka | 526/178 X |
| 3,555,066 | 1/1971 | Grow | 526/178 X |
| 3,769,266 | 10/1973 | Nametkin et al. | 526/178 |
| 3,929,850 | 12/1975 | Streck et al. | 526/143 X |
| 4,098,808 | 7/1978 | Wolfers et al. | 260/448.8 |
| 4,145,507 | 3/1979 | Wolfers et al. | 528/25 |
| 4,351,924 | 9/1982 | Andrews et al. | 525/330.6 |
| 4,730,031 | 3/1988 | Sato et al. | 526/279 |
| 4,866,145 | 9/1989 | Dicker | 526/190 |
| 5,081,191 | 1/1992 | Quirk | 526/279 X |
| 5,153,291 | 10/1992 | Leitz et al. | 526/279 |

FOREIGN PATENT DOCUMENTS 0189174 7/1986 European Pat. Off. .
2632294C2 7/1976 Fed. Rep. of Germany .
2615039 10/1977 Fed. Rep. of Germany .

OTHER PUBLICATIONS

Polymer Preprints, American Chemical Society, vol. 27, No. 1, 1986 S. Nakahama "Anionic Living Polymerization of Protected Functional Monomers".

Primary Examiner—Fred Teskin
Attorney, Agent, or Firm—Nixon & Vanderhye

[57] ABSTRACT

Process for anionically polymerising a conjugated 1,3-diene monomer consists of contacting the monomer in an inert hydrocarbon solvent with a monofunctional silyl ether initiator of general formula $R^1R^2R^3Si$—O—A—Li where $R^1$ to $R^3$ are independently selected from monovalent organic substituent groups and A is a short chain hydrocarbon bridging group, to yield a polydiene having a molecular weight of typically 1,000–10,000, a high 1.4 content of typically 90% and a low polydispensity of typically 1.15. The reactive ends of the living polymer chains may be terminated with a reactive group such as hydroxyl by treating the polymer with ethylene oxide. Subsequent removal of the polymer's relatively unreactive silyl end groups by reaction with tetra-n-butylammonium fluoride produces a difunctional, chain-extendable, hydroxy-terminated polydiene useful as a rubbery binder prepolymer.

9 Claims, No Drawings

POLYMERIZATION OF OLEFINIC-CONTAINING MONOMERS EMPLOYING ANIONIC INITIATORS

This invention relates to a process for the polymerisation of olefinic-containing monomers employing anionic initiators. The invention also relates to novel anionic initiators for use in said process, and to polymers produced by said process.

Highly useful polymeric products can be obtained by polymerising olefinic-containing monomers in the presence of an organo-alkali metal initiator and subsequently reacting the resulting polymer, containing an active alkali metal end group or groups, with a reagent which will either couple the polymer molecules or replace the alkali metal with more stable reactive end groups.

It can be seen that such a polymerisation process will consist essentially of three stages:

a. Initiation, in which the monomeric material is contacted with a monofunctional or difunctional anionic initiator.

b. Propagation, in which the monomer is allowed to polymerise to form living polymer chains with negatively charged ends, and c. Terminator, in which the living polymer chains are treated with suitable reagents, generally to form monofunctionally or difunctionally terminated polymers.

The presence of a reactive terminal group or groups on the ends of the polymer molecules enables substantially more effective cures to take place. In the case of a polymer containing a reactive group on each of its ends (a telechelic polymer) all of the polymer molecule will be tied into the cross-linked structure of the cured material.

The well defined structure produced by telechelic polymers in the networks of their cured products is the primary reason for their increased use as precursors in the commercial production of cured rubbery solids.

However, in order to meet the requirements of a modern synthetic rubber it is not enough that the polydiene produces effective cures nor that the cured product has a well defined cross linked structure, it is also important that the cured product possesses good elastomeric properties. In the case of polydienes the elastomeric quality of the cured product is dependent upon the 1,4-content of the polymeric diene. Generally, the higher the 1,4-content of the polymer, the lower its glass transition temperature and the better the elastomeric properties of the cured product. It follows from this that any process chosen for the commercial production of polydienes (in particular telechelic polymers of 1,3-dienes) must lead to a material having a high 1,4-content.

It is well known that monofunctional polyalkenes and high 1,4-content monofunctional polydienes can be prepared in inert non-polar hydrocarbon solvents by initiating the reaction with a monofunctional anionic initiator such as butyl lithium. The preparations of telechelic polydienes, using corresponding difunctional initiators such as 1,4-dilithiobutane, has hitherto required that the anionic polymerisation reaction (propagation) takes place in the presence of a sterically-hindered Lewis acid in order to ensure that the polymeric product possesses a reasonable 1,4-content (typically 25-50%). Furthermore, the polymerisation reaction must take place in polar solvents such as alkyl and cycloalkyl ethers because difunctional initiators are insoluble in non-polar solvents such as hydrocarbons, and this has hitherto prevented the formation of polydienes with 1,4-contents above about 50% which can be produced using the aforementioned monofunctional initiators in hydrocarbon solvents.

A further disadvantage associated with the use of difunctional initiators is that the choice of telechelic polymers which can be produced at the termination of propagation is restricted to those having identical terminal groups at either end since the reagent used for termination will react in a similar manner with both living ends of the growing polymer chain.

The main object of the present invention is to provide a new process for the anionic polymerisation of an olefinic-containing monomer which can be used to prepare telechelic polymers and yet avoids the disadvantages associated with the use of known difunctional initiators. It is a further object of the present invention to provide a process for the anionic polymerisation of a conjugated 1,3-diene which produces a polymeric material having an enhanced 1,4-content. It is a yet further object of the invention to provide a novel anionic initiator for use in the present process.

According to the present invention, there is provided a process for the anionic polymerisation of an olefinic-containing monomer comprising contacting the monomer in an inert solvent with a monofunctional silyl ether initiator of general formula I

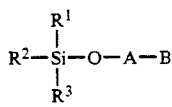

$$R^2-\underset{\underset{R^3}{|}}{\overset{\overset{R^1}{|}}{Si}}-O-A-B \qquad I$$

wherein $R^1$, $R^2$ and $R^3$ are independently selected from saturated and unsaturated aliphatic and aromatic radicals, A is a hydrocarbon bridging group containing from 1 to 25 carbon atoms and B is an alkali metal.

The inert solvent is preferably a non-polar solvent such as a hydrocarbon, since anionic polymerisation in the presence of such solvents is known to produce, from 1,3-dienes, polydienes with high 1,4-contents. Preferred solvents are aliphatic, alicyclic and aromatic hydrocarbons, especially alkanes, cycloalkanes and cycloalkenes, having from 3 to 12, preferably from 4 to 8, carbon atoms. Examples of suitable hydrocarbons are hexane, cyclohexane, toluene and benzene. Alkanes are the most preferred solvents.

The olefinic monomer is preferably an alkene or a 1,3-diene. The alkene or 1,3-diene will be chosen from the group of unsaturated organic compounds that can be polymerised anionically (i.e. in a reaction initiated by an organo alkali metal). Suitable alkenes include the optionally-substituted styrenes and vinylnaphthalenes. Suitable 1,3-dienes will preferably contain from 4 to 12, especially from 4 to 8, carbon atoms per molecule. Examples of these compounds include the following: 1,3-butadiene; isoprene; 2,3-dimethyl-1,3-butadiene; 1,3-pentadiene; 2-methyl-3-ethyl-1,3-butadiene; 3-methyl-1,3-butadiene; 2-methyl-3-ethyl-1,3-pentadiene; 1,3-hexadiene; 2-methyl-1,3-hexadiene; 1,3-heptadiene; 3-methyl-1,3-heptadiene; 1,3-octadiene; 3-butyl-1,3-octadiene; 3,4-dimethyl-1,3-hexadiene; 3-n-propyl-1,3-pentadiene; 4,5-diethyl-1,3-octadiene; phenyl-1,3-butadiene; 2,4-diethyl-1,3-butadiene; 2,3-di-n-propyl-1,3-butadiene; and 2-methyl-3-isopropyl-1,3-butadiene.

Among the dialkylbutadienes, it is preferred that the alkyl groups contain from 1 to 3 carbon atoms. Of the above monomers 1,3-butadiene, isoprene, 2,3-dimethyl-1,3-butadiene and 1,3-pentadiene are preferred with 1,3-butadiene being particularly preferred. The dienes may be polymerised alone, or in admixture with each other or with alkenes to form random copolymers, or by charging the dienes to the reaction mixture sequentially, either with each other or with alkenes, to form block copolymers.

$R^1$, $R^2$ and $R^3$ are preferably independently selected from alkyl, aryl, and alkaryl. More preferably, each of the radicals $R^1$, $R^2$ and $R^3$ contains from 1 to 10 carbon atoms. In order to reduce the reactivity of the siloxy group on the initiator, the radicals $R^1$, $R^2$ and $R^3$ are preferably not all methyl and preferably together contain at least 4, most preferably at least 5, carbons atoms. In this way, a degree of steric hindrance is introduced into the silyl group which inhibits reaction between that group and the living ends of the growing polymer chain, especially when at least one of $R^1$, $R^2$ and $R^3$ contain at least three, more especially at least four, carbon atoms. Polymer yield and purity is also generally enhanced if at least one of $R^1$, $R^2$ and $R^3$ is aryl, preferably phenyl or mono-substituted phenyl with the mono-substituent group on the phenyl preferably being a $C_1$-$C_5$ alkyl group.

The spacer group A is preferably contains at least two carbon atoms and is preferably a saturated hydrocarbon group such as a branched or straight chain alkyl bridging group, though less preferably it may contain at least one aromatic group such as a p-phenylene group. The principal criteria for the selection of the group A is that it should be sufficiently long to prevent the siloxy end group from interfering with the polymerisation reaction, and it should provide the initiator with enhanced solubility in the inert, preferably non-polar solvent employed in the process. At the same time it should not add significantly to the size and bulk of the terminal group at the end of the polymer chain because this will adversely affect the polymer's physical properties, especially its elastomeric properties. For these reasons, A is most preferably a straight chain alkyl bridging group of formula —$(CH_2)$—$_m$ where m is an integer from 3 to 15, especially 3 to 10.

B is preferably lithium or sodium, and is most preferably lithium.

The present polymerisation reaction is preferably carried out at a temperature of between $-31°$ C. and $+30°$ C., especially between $10°$ C. and $+10°$ C. The maximum temperature that may be employed in a given system will depend primarily on the physical properties, especially the boiling points, of the monomers and solvent chosen.

The amount of initiator added to the reaction mixture will be determined by the structure of the monomer to be polymerised and by the desired molecular weight of the polymer. Typically for the production of a polymer containing a polymeric chain, derived from the polymerisation of an olefinic-containing monomer and having a polymer molecular weight between about 1,000 and 100,000, between 0.5 and 50 mmoles of initiator is used for each mole of monomer. The polymeric chain preferably has a molecular weight in the range 1,000 to 10,000 in which case preferably between 5 and 50 mmoles of initiator is used for each mole of monomer.

After propagation has been allowed to reach equilibrium, the single active ends on the living polymer chains may be terminated, by the addition of suitable reagents which either donate a proton to or functionalise the anionic carbons. Proton donors such as water or alcohol yield terminally non-functional polymers. Preferably, however, the polymer chains will be terminated by a functional group. Examples of suitable end groups are:

a. hydroxyl, prepared by adding aldehydes, ketones or alkylene oxides, especially ethylene oxide;

b. carboxyl, prepared by adding $CO_2$ to the anionic polymer;

c. mercapto, prepared by adding sulphur, cyclic disulphides or cyclic sulphides such as ethylene or propylene sulphides;

d. amino and aziridine, prepared by adding aminoaldehydes or polyaziridines such as phenyl-bis(2-methyl-1-aziridinyl) phosphine oxide;

e. epoxide, prepared by adding glycidaldehyde or diepoxides; and f. metal halides, especially magnesium halides, prepared by adding a metal halide such as magnesium bromide.

Alternatively, the living polymer chains may be terminated by a di-or polyfunctional coupling agent which is capable of terminating two or more polymer chains through a single coupling agent molecule, thereby linking those chains together, with the advantage that a considerable increase in polymer molecular weight can be achieved with little degradation in polydispersivity. An example of such a coupling agent is $SiCl_4$, which by displacement of its chloro substituent groups yields a "star" polymer with four, organosiloxy-terminated polymer chains radiation from a central silicon atom. Other polymers containing from 2 or 3 to 20 polymer chain arms radiating from a central coupling agent may be prepared utilising complex coupling agents such as multi-functional organohalides typically containing from 2 or 3 to 20, preferably 2 to 4, halide groups, and other multi-functional polyhalosilanes preferably containing from 2 to 4 halide groups. Examples of such coupling agents are 1,2 ethylene dibromide, 1,4 dichlorobutane, and dimethyldichlorosilane.

The organosiloxy protective groups remain unaffected by these various termination reactions. However, once propagation has been terminated, the relatively inert organosiloxy end groups on the polymer chains may then be functionalised by reaction with a desilylation reagent to yield, after subsequent reaction with acid solution, reactive hydroxyl end groups which are reactive in the sense that they can be reacted further to give rise to chemical cross-linking of the polymer chains. Preferred reagents for such desilylation reactions are the tetralkylammonium fluorides, especially tetra-n-butylammonium fluoride, in polar solvents such as alkyl or cycloalkyl ethers, especially tetrahydrofuran. These and other suitable desilylation reagents are discussed in Synthesis, 9, 817-845 (1985), especially on page 828. Since aziridine and epoxide groups may react with some of these reagents and/or acid solutions, these groups represent less preferred terminal groups on the other ends of the polymer chains prior to desilylation.

The present polymerisation process offers a number of significant advantages over other known anionic polymerisation processes. First, the molecular weight distribution ($M_w/M_n$) is narrower than that achieved by the analogous reaction using difunctional anionic initiators. In the present case the molecular weight distribution (also known as "polydispersivity") is typically about 1.1 whilst in the competing process $M_w/M_n$ is for a polydiene generally 1.5 or above in the absence of sterically-hindered Lewis acid and about 1.3 in the presence of a sterically-hindered Lewis acid. The advantage offered by a polymer with a narrow $M_w/M_n$ is that it produces a cured product with a well defined network and, as a consequence, high strength.

The second advantage offered by the present process is the enhancement of the 1,4-content of the polydiene products it is capable of producing from the anionic polymerisation of 1,3-dienes. In the present process, polydienes with a 1,4-content of 90% can be routinely prepared, whereas with difunctional initiators, the maximum 1,4-contents achievable is about 50%. This advantage stems principally from the advantageous solubility of the present initiator compounds in inert, non-polar hydrocarbon solvents which obviates the need to conduct polymerisation within a polar solvent.

A third advantage of the present invention is that it allows for the preparation of polymers with a far greater diversity of functionality than has hitherto been achievable by anionic polymerisation. Monofunctional polymers result from termination with a proton donor followed by reactive functionalisation of the organosiloxy end groups (for example, to produce reactive hydroxyl end groups). Bifunctional (telechelic) polymers result from (a) functional termination of the polymerisation reaction followed by (b) reactive functionalisation of the organosiloxy end groups. Indeed this can lead to telechelic polymers having the same or different functional end groups depending on the reagents used in each of the steps (a) and (b), adding further to the aforesaid advantage of diversity. Di- and poly-functional polymers result from termination of the polymerisation reaction with di- and poly-functional coupling agents, followed by reactive functionalisation of the organosiloxy end groups.

The monofunctional silyl ether initiators which are used in the present process are preferably prepared by the method of reacting, in an inert solvent, the alkali metal B with an organosiloxyhalide of formula II

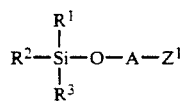
II wherein $R^1$, $R^2$, $R^3$ and A are as defined above and $Z^1$ represents a halogen. The reaction may be represented by the equation

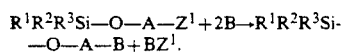

$Z^1$ is preferably chlorine or bromine, and is most preferably chlorine.

The reaction, which is exothermic, is preferably performed in a non-polar solvent. Preferred solvents are aliphatic, alicyclic and aromatic hydrocarbons, especially alkanes, cycloalkanes and cycloalkenes, having from 3-12, preferably from 4-8, carbon atoms. Most preferably, the solvent is the same as that used in the subsequent polymerisation reaction.

The alkali metal B, which is preferably lithium, is preferably provided in particulate form such as chopped fine wire (typically 1-2 mm diameter) or freshly cut chips. The particles are preferably subjected to high speed agitation in a fluid suspension prior to use to produce a clean metallic surface for further reaction. If lithium is used, then it preferably contains from 0.5-3%, more preferably 1-2%, by weight of sodium. In the absence of sodium, lithium tends to be unreactive towards organic halides. However, with increasing sodium content, there is an increasing likelihood of undesirable side reactions and above 5 wt % sodium, the reagents may react violently. It has been found that in order to ensure a high yield of product initiator, a stoichiometric excess of alkali metal must be used, of preferably at least 1½-fold, more preferably at least two-, fold, most preferably at least 2½-fold, with an upper limit of preferably six-fold.

The reaction is preferably performed at a temperature of from 10° C. to 50° C., more preferably from 20° C. to 40° C. At temperatures above about 40° C., the production of undesirable organic by-products is observed. The temperature can be controlled by cooling the reaction, and by ensuring that the major part of the organosiloxyhalide co-reagent is added slowly to the alkali metal already in situ within the solvent. A reaction temperature of at least 30° C. is most preferred especially if the solvent is non-polar, to ensure that the reaction goes substantially to completion.

A further preferred condition of the reaction is that it should be performed under a dry, oxygen-free inert gas. The gas is preferably a noble gas such as helium or argon, since nitrogen will react with the alkali metal to form a metal nitride, especially if the metal is lithium.

The advantage of this method of initiator preparation is that the principal by-products of the reaction (alkali metal halide and excess alkali metal) are insoluble inorganic solids rather than reactive, solvent-soluble organic compounds and so are easily separated from the soluble initiator compound before it is used in the subsequent polymerisation process.

The organosiloxyhalide compound of general formula II may be prepared by reacting, in an inert solvent an alcohol of general formula III

III with a silylhalide of general formula IV

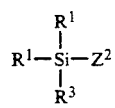
IV wherein $Z^2$ is a halogen which is the same or different to $Z^1$ and is preferably chlorine.

The terminated polymers resulting from the present process represent a novel group of polymers which may be used as intermediates in the preparation of further, functionally terminated polymers, especially telechelic polymers, by the subsequent conversion of the protective organosiloxy end groups into hydroxyl functional groups.

According to a second aspect of the present invention, therefore, there is provided a siloxy-terminated hydrocarbon polymer containing at least one polymer chain per molecule of general formula V

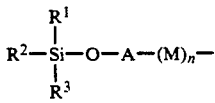

wherein $R^1$, $R^2$, $R^3$ and A are as defined above, and $-(M)_n-$ represents a polymerised olefinic-containing monomer, preferably a polymerised alkene or, more preferably, a polymerised 1,3-diene.

The polymer may be of general formula VI

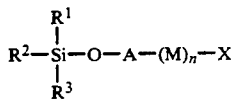

wherein X is selected from H, carboxyl, hydroxyl, mercapto, amino and a metal halide, especially a magnesium halide, group. Such polymers are produced by terminating the living polymer chain produced by the present process by the monofunctional reagents described above. Alternatively, the polymer may be of general formula VII

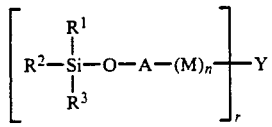

wherein Y is the residue of a di- or multi-functional halide coupling agent containing q functional halide groups, where q is an integer from 2 to 20 (for example, 3), especially from 2 to 4, and r is an integer of at least 2 (for example, 3) which is less or equal to q. For example, four-chain polymers of general formula VII linked together by a single silicon atom can be produced by living chain termination with the polyfunctional coupling agent $SiCl_4$. Similarly, polyfunctional organohalide coupling agents such as 1, 2 ethylene dibromide and 1,4 dichlorobutane, and other polyfunctional polyhalosilane coupling agents such as dimethyldichlorosilane, may also be used.

Preferably, the polymeric chain $-(M)_n-$ has an average molecular weight in the range of 1,000 to 10,000, especially 2,000 to 7,000 in which case the polymers produced by the present invention will, if the polymer molecules contain a single polymeric chain $-(M)_n-$, normally be liquids. If desired however semisolid and solid polymers with polymeric chains $-(M)_n-$ having an average molecular weight of up to 100,000 or above may also be prepared.

The present invention will now be described by way of Example only.

MATERIALS

Butadiene (Matheson) was dried by passage through molecular sieves, calcium chloride and calcium hydride, before collecting in a graduated vessel at $-78°$ C.

Diethylether (BDH) was dried overnight over freshly cut sodium metal (2 mm diameter wire), filtered and used immediately.

Diphenylacetic acid (BDH) was stored at 40° C. under vacuum for at least 24 hours before use.

Hexane (BDH) was dried over calcium hydride and fractionally distilled under nitrogen, the fraction boiling at 67°-8° C. being collected. Lithium metal (Fluke) containing 1-2% sodium was supplied as a 30% w/w dispersion in mineral oil. The metal was washed repeatedly with hexane before charging with the reaction solvent so as to prepare a clean silvery white metal surface.

Tert-butyldimethylsiloxy 1-chloro-hexyl ether was fractionally distilled, under reduced pressure prior to use, the fraction boiling at 184°-5° C. (100 mmHg) being collected.

Tert-butyldiphenylsiloxy 1-chloro-hexyl ether was distilled from a kugelrohr (oven temperature 215° C.) under reduced pressure (1 mmHg), just prior to use.

Terta-butyldiphenylsiloxy 1-chloro-propyl ether was distilled from a kugelrohr (oven temperature 200° C.) under reduced pressure (1 mmHg), just prior to use.

Tetra-n-butylammonium fluoride (Aldrich) was supplied as a 1.0M solution in tetrahydrofuran and used directly.

Tetrahydrofuran (BDH), stabilised with 0.1% quinol, was distilled under nitrogen when required after sufficient sodium benzophenone solution in THF had been added to yield a permanent purple colour.

GENERAL PROCEDURE

All experimental techniques were performed under an inert atmosphere, be it oxygen-free nitrogen or argon. All glassware, except syringes, was cleaned by successive washing with 10% hydrofluoric acid, distilled water and acetone. It was then dried and stored in an oven at 120° C. until required. All additions, excepting that of alkali metals, were performed via syringe.

EXAMPLE 1

A sixfold excess of lithium slurry (10 g) in mineral oil was placed into a 500 ml 3-necked round bottom flask equipped with serum cap, argon inlet/outlet, water condenser, thermometer and magnetic follower. The slurry was then repeatedly washed with hexane, by high speed agitation, until a clean silvery white metal surface was obtained. The lithium metal was then charged with further hexane (100 ml) which was to act as the reaction solvent. The temperature inside the reaction flask was then raised to 35° C. and allowed to reach thermal equilibrium over the space of thirty minutes.

Freshly distilled tert-butyldimethyl (tBDM-) siloxy-1-chlorohexyl ether (5 g, 0.02 mol) was injected into the reaction vessel. A primary exotherm was observed to commence after 5-10 minutes. This exotherm was controlled by the utilisation of cold air cooling which maintained the flask temperature below 45° C. throughout the course of the reaction. Four further aliquots of tBDM-siloxy-1-chlorohexyl ether (4×5 g, 0.08 mol) were added over a period of 1-2 hours. The reaction was allowed to proceed for a further 2 hours before allowing the products to settle inside the flask. The crude supernatant hexane solution of tBDM-siloxy-1-lithiohexyl ether could then be extracted via syringe and utilised in various reactions, or simply quenched with methanol to produce tBDM-siloxy hexane (Yield 95%). The yield of the reaction was confirmed by $^1H$ n.m.r. spectroscopy and i.r. spectroscopy.

EXAMPLE 2

The procedure of Example 1 was repeated except that the species to be lithiated was tert-butyldiphenyl (t-BDP-) siloxy-1-chlorohexyl ether rather than tertbutyldimethylsiloxy-1-chlorohexyl ether. The resultant yield of the reaction was again greater than 90%.

EXAMPLE 3

The procedure of Example 1 was repeated except that the reaction was executed within the temperature range 20°–30° C., and the reaction solvent was diethylether instead of n-hexane. The resultant yield of the reaction was again greater than 90%.

EXAMPLE 4

The procedure of Example 1 was repeated except that the species to be lithiated was tert-butyldiphenylsiloxy-1-chloropropyl ether rather than tert-butyldimethylsiloxy-1-chlorohexyl ether. The reaction was executed within the temperature range 20°–30° C., and the reaction solvent was diethylether instead of n-hexane. The resultant yield of the reaction was again greater than 90%.

EXAMPLE 5

The procedure of Example 1 was repeated except that the species to be lithiated was tert-butyldiphenylsiloxy-1-chloropropyl ether rather than tert-butyldimethylsiloxy-1-chlorohexyl ether. The reaction was executed within the temperature range 20°–30° C. The resultant yield of the reaction was only 25% after 17 hours.

TABLE 1

The Effect of Temperature and Solvent Upon the Preparative Yield of Trialkyl/aryl Siloxy Lithioalkyl Ethers

| Trialkyl/Arylsiloxy Lithioalkyl Ether | Solvent | Temperature | Yield |
|---|---|---|---|
| tBDM-siloxy lithiohexyl ether | Hexane | 35–40° C. | >90% |
| " | Ether | 20–30° C. | >90% |
| tBDP-siloxy | Hexane | 35–40° C. | >90% |
| tBDP-siloxy lithiopropyl ether | Ether | 20–30° C. | >90% |
| " | Hexane | 20–30° C. | 25% |

EXAMPLE 6

Hexane (250 ml) was placed in a 500 ml round bottom 3-necked flask equipped with magnetic follower, thermometer, serum cap and nitrogen inlet/outlet. The reaction vessel was then chilled to −78° C. and butadiene (30 ml) was distilled into the system. The reaction mixture was then gradually allowed to warm to −5° C. and tBDM-siloxy 1-lithiohexyl ether (0.011 mol) in hexane solution from Example 1 was introduced by injection in order to initiate polymerisation. Propagation was allowed to proceed at this temperature for an hour, before the ice bath was removed and the reaction mixture gradually allowed to reach room temperature. Propagation was then allowed to continue at room temperature for a further 16 hours. Termination of the living ends was then accomplished typically by the injection of a five-fold excess of methanol (1 ml) to yield a water white polymer solution. This was subsequently reduced in volume by rotary evaporation, precipitated into excess methanol (1000 ml) and the crude polymer syrup collect on decanting. The work up produced a monofunctional polybutadiene with a siloxyl group on one end of the polymer chain. The product was found to be of low molecular weight (2,100., to be relatively monodisperse ($M_n/M_w$=1.1) and to possess a high 1.4 percentage content (89%).

The molecular weight of the product was determined by gel permeation chromatography (gpc) in which measurements were carried out using a Waters 840 chromatograph fitted with refractive index and ultra-violet detectors in series. Four styragel columns (Polymer Laboratories) of porosity $10^5$Å, $10^4$Å, $10^3$Å and $10^2$Å were used, and the molecular weight was determined from a universal polystyrene calibration curve using the Mark-Houwinck co-efficients a=0.693, K=4.03×$10^{-4}$ (high 1,2) and K=4.57×$10^{-4}$ (high 1,4).

The percentage 1,4 content of the product was determined by $^1$H nuclear magnetic resonance (nmr) spectroscopy in which measurements were carried out on a Varian Associates EM 60 MHz spectrometer, samples of the polymer being prepared as 10% w/v solutions in deuterochloroform.

EXAMPLE 7

The procedure of Example 6 was repeated except the reaction was initiated with tBDP-siloxy lithiohexyl ether from Example 2 rather than with tBDM-siloxy lithiohexyl ether.

EXAMPLE 8

The procedure of Example 6 was repeated except that the reaction was terminated with excess ethylene oxide rather than excess methanol. The usual work up procedure produced a bifunctional polybutadiene, with a hydroxyl group at one end of the chain and a siloxyl group at the other.

EXAMPLE 9

The procedure of Example 6 was repeated except that the reaction was terminated with exactly 0.0055 mol of dichlorodimethylsilane rather than excess methanol. The usual workup procedure produced a difunctional polybutadiene ($M_n/M_w$ between 1.1 and 1.2 and % 1,4 content between 87% and 91%) possessing siloxyl groups at both ends and a central dimethylsilyl chain-linking group.

EXAMPLE 10

Siloxyl terminated polybutadiene (1 g) from Example 6 was dissolved in tetrahydrofuran (20 ml) in a 100 ml round bottom 3-necked flask equipped with magnetic follower, serum cap and nitrogen inlet/outlet. Tetra-n-butylammonium fluoride (1.0M) in tetrahydrofuran (1.1 ml) was then added by injection and the reaction allowed to proceed at 20° C. for 2 hours. Afterwards the solution was added dropwise to excess methanol, allowed to settle and the liquors decanted off to yield a pale yellow syrup, which was identified as monofunctional hydroxyl terminated polybutadiene ($M_n/M_w$=1.15, and % 1,4 content=90%).

EXAMPLE 11

The procedure of Example 10 was repeated using as the starting polymer the siloxy-terminated polybutadiene products of Example 7 rather than the product of Example 6, to yield a monofunctional hydroxy-terminated polybutadiene ($M_n/M_w$ between 1.1 and 1.2, and % 1,4 content between 87% and 91%).

EXAMPLES 12 AND 13

The procedure of Example 10 was repeated using as the starting polymer the siloxy-terminated polybutadiene products of Examples 8 and 9 in turn rather than the product of Example 6. In both cases, the siloxy groups on the starting polymers were replaced by hydroxy groups, to yield difunctional hydroxy-terminated polybutadienes ($M_n/M_w$ between 1.1 and 1.2, % 1,4 content between 87% and 91%).

We claim:

1. Process for the anionic polymerisation of an olefinic-containing monomer comprising contacting the monomer in an inert solvent with a monofunctional silyl ether initiator of the formula I

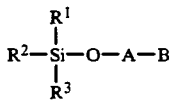     I wherein $R^1$, $R^2$ and $R^3$ are independently selected from saturated and unsaturated aliphatic and aromatic radicals, A is a hydrocarbon bridging group containing from 1 to 25 carbon atoms, and B is an alkali metal.

2. Process according to claim 1 wherein the monomer comprises a 1,3-diene.

3. Process according to claim 1 wherein each of $R^1$, $R^2$ and $R^3$ contains from 1 to 10 carbon atoms and $R^1$, $R^2$ and $R^3$ together contain at least 5 carbon atoms.

4. Process according to claim 1 wherein —A— is —$(CH_2)_m$— where m is an integer from 3 to 15.

5. Process according to claim 1 wherein, after propagation has ceased, the living polymer chains are terminated by a proton or a functional group, or are linked together by a di- or poly-functional linking agent.

6. Process according to claim 5 wherein the functional group is selected from carboxyl, hydroxyl, mercapto, amino, and a metal halide.

7. Process according to claim 5 wherein the linking agent comprises a halosilane or an organohalide.

8. Process according to claim 5 wherein, after the living polymer chains are terminated or linked together, the organosiloxy terminal groups on the polymer chains are desilylated and protonated to convert said groups into functional hydroxyl groups.

9. A siloxy-terminated hydrocarbon polymer containing at least one polymer chain per molecule of the formula:

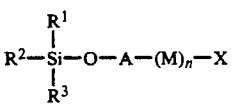

wherein $R^1$, $R^2$, $R^3$ are independently selected from saturated and unsaturated aliphatic and aromatic radicals, A is a saturated hydrocarbon bridging group optionally containing at least one aromatic group, —$(M)_n$— represents a polymer of an olefinic containing monomer, n has a value such that the average molecular weight of the polymeric chain is from about 1,000 to about 100,000, and X is selected from carboxyl, hydroxy, mercapto, amino, and a metal halide group.

* * * * *

REEXAMINATION CERTIFICATE (3956th)

United States Patent [19]
Shepherd et al.

[11] B1 5,331,058
[45] Certificate Issued Dec. 14, 1999

[54] POLYMERIZATION OF OLEFINIC-CONTAINING MONOMERS EMPLOYING ANIONIC INITIATORS

[75] Inventors: Neil Shepherd, Waltham Abbey; Malcolm J. Stewart, Henlow, both of United Kingdom

[73] Assignee: The Secretary of State for Defence in Her Britannic Majesty's Government of the United Kingdom of Great Britain and Northern Ireland, Whitehall, United Kingdom

Reexamination Request:
  No. 90/005,163, Nov. 18, 1998

Reexamination Certificate for:
  Patent No.: 5,331,058
  Issued: Jul. 19, 1994
  Appl. No.: 07/920,368
  Filed: Aug. 17, 1992

[22] PCT Filed: Feb. 6, 1991
[86] PCT No.: PCT/GB91/00187
  § 371 Date: Aug. 17, 1992
  § 102(e) Date: Aug. 17, 1992
[87] PCT Pub. No.: WO91/12277
  PCT Pub. Date: Aug. 22, 1991

[30] Foreign Application Priority Data
  Feb. 8, 1990 [GB] United Kingdom .................. 9002804

[51] Int. Cl.$^6$ ................ C08F 8/42; C08F 8/34; C08F 8/32; C08F 4/46
[52] U.S. Cl. .................. 525/332.3; 525/333.2; 525/343; 525/348; 525/359.1; 525/360; 525/367; 525/383; 525/379; 525/385; 525/386; 526/173; 526/178; 526/335; 526/348
[58] Field of Search .................. 526/178, 335, 526/348; 525/379, 332.3, 333.2, 343, 348, 359.1, 360, 367, 383, 385, 386

[56] References Cited

FOREIGN PATENT DOCUMENTS 63-218704  9/1988  Japan.

*Primary Examiner*—Fred M. Teskin

[57] ABSTRACT

Process for anionically polymerising a conjugated 1,3-diene monomer consists of contacting the monomer in an inert hydrocarbon solvent with a monofunctional silyl ether initiator of general formula $R^1R^2R^3Si$—O—A—Li where $R^1$ to $R^3$ are independently selected from monovalent organic substituent groups and A is a short chain hydrocarbon bridging group, to yield a polydiene having a molecular weight of typically 1,000-10,000, a high 1.4 content of typically 90% and a low polydispensity of typically 1.15. The reactive ends of the living polymer chains may be terminated with a reactive group such as hydroxyl by treating the polymer with ethylene oxide. Subsequent removal of the polymer's relatively unreactive silyl end groups by reaction with tetra-n-butylammonium fluoride produces a difunctional, chain-extendable, hydroxy-terminated polydiene useful as a rubbery binder prepolymer.

REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 9 are determined to be patentable as amended.

Claims 2–8, dependent on an amended claim, are determined to be patentable.

1. Process for the anionic polymerisation of an olefinic-containing monomer comprising contacting the monomer in an inert solvent with a monofunctional silyl ether initiator of the formula I

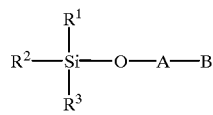

wherein $R^1$, $R^2$ and $R^3$ are independently selected from saturated and unsaturated aliphatic and aromatic radicals, A is [a] *an aliphatic* hydrocarbon bridging group containing from 1 to 25 carbon atoms, and B is an alkali metal.

9. A siloxy-terminated hydrocarbon polymer containing at least one polymer chain per molecule of the formula:

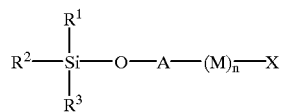

wherein $R^1$, $R^2$, $R^3$ are independently selected from saturated and unsaturated aliphatic and aromatic radicals, A is a saturated *aliphatic* hydrocarbon bridging group [optionally containing at least one aromatic group], $—(M)_n—$ represents a polymer of an olefinic containing monomer, n has a value such that the average molecular weight of the polymeric chain is from about 1,000 to 100,000 and X is selected from carboxyl, hydroxy, mercapto, amino, and a metal halide group.

* * * * *